(12) United States Patent
Viebach et al.

(10) Patent No.: US 10,874,291 B2
(45) Date of Patent: Dec. 29, 2020

(54) FLUID BLOCK FOR AN ENDOSCOPE CONTROL PART AND ENDOSCOPE

(71) Applicant: Digital Endoscopy GmbH, Friedberg (DE)

(72) Inventors: Thomas Viebach, Waidhofen (DE); Fritz Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 248 days.

(21) Appl. No.: 15/113,801

(22) PCT Filed: Jan. 22, 2015

(86) PCT No.: PCT/EP2015/051252
§ 371 (c)(1),
(2) Date: Jul. 22, 2016

(87) PCT Pub. No.: WO2015/110528
PCT Pub. Date: Jul. 30, 2015

(65) Prior Publication Data
US 2016/0338577 A1    Nov. 24, 2016

(30) Foreign Application Priority Data

Jan. 23, 2014   (DE) .................. 10 2014 201 208

(51) Int. Cl.
*A61B 1/015*    (2006.01)
*A61B 1/00*     (2006.01)
*A61B 1/12*     (2006.01)

(52) U.S. Cl.
CPC .......... *A61B 1/015* (2013.01); *A61B 1/00066* (2013.01); *A61B 1/00105* (2013.01);
(Continued)

(58) Field of Classification Search
CPC ... A61B 1/0125; A61B 1/015; A61B 1/00064; A61B 1/00066; A61B 1/00068;
(Continued)

(56) References Cited

U.S. PATENT DOCUMENTS 3,549,806 A    12/1970  Wood
3,605,725 A     9/1971  Bentov
(Continued)

FOREIGN PATENT DOCUMENTS

CN      1286664 A    3/2001
CN    102697445 A    7/2002
(Continued)

OTHER PUBLICATIONS

JP2010125019A English Translation Attached (Year: 2010).*
(Continued)

*Primary Examiner* — Ryan N Henderson
*Assistant Examiner* — Pamela F Wu
(74) *Attorney, Agent, or Firm* — Knobbe, Martens, Olson & Bear, LLP

(57) ABSTRACT

The invention relates to a fluid block (1) for an endoscope operating element, comprising at least one gas-conducting channel (4) provided inside the fluid block (1) and having an inlet opening and an outlet opening, at least one liquid-conducting channel (5) provided inside the fluid block (1) and having an inlet opening and an outlet opening, and at least one control valve (2) for opening/blocking the at least one gas-conducting channel (4) and the at least one liquid-conducting channel (5).
The invention further relates to an endoscope having such a fluid block.

13 Claims, 6 Drawing Sheets

(52) U.S. Cl.
CPC ...... *A61B 1/00114* (2013.01); *A61B 1/00137* (2013.01); *A61B 1/125* (2013.01); *A61B 1/00103* (2013.01)

(58) Field of Classification Search
CPC ............ A61B 1/00119; A61B 1/00128; A61B 1/00131; A61B 1/00137; A61B 1/273
USPC ................................. 600/157–159, 109, 131
See application file for complete search history.

(56) References Cited

U.S. PATENT DOCUMENTS

| | | | |
|---|---|---|---|
| 4,241,729 | A | 12/1980 | Aoshiro |
| 4,404,963 | A | 9/1983 | Kohri |
| 4,415,767 | A | 11/1983 | Gill et al. |
| 4,670,009 | A | 6/1987 | Bullock |
| 5,245,133 | A | 9/1993 | DeCarlo et al. |
| 5,569,157 | A | 10/1996 | Nakazawa et al. |
| 5,588,950 | A | 12/1996 | Sano |
| 5,630,419 | A | 5/1997 | Ranalletta |
| 6,334,844 | B1 | 1/2002 | Akiba |
| 6,383,132 | B1* | 5/2002 | Wimmer ............ A61B 1/00068 600/101 |
| 6,547,722 | B1 | 4/2003 | Higuma et al. |
| 6,582,361 | B2 | 6/2003 | Hirano |
| 6,716,160 | B2 | 4/2004 | Mitsumori |
| 7,179,223 | B2 | 2/2007 | Motoki et al. |
| 7,198,599 | B2 | 4/2007 | Goto et al. |
| 7,841,880 | B2 | 11/2010 | Ikeda |
| 2001/0025135 | A1 | 9/2001 | Naito et al. |
| 2002/0040180 | A1 | 4/2002 | Hirano |
| 2002/0115907 | A1 | 8/2002 | Mitsumori |
| 2003/0032862 | A1* | 2/2003 | Ota .................... A61B 1/00068 600/158 |
| 2003/0092965 | A1 | 5/2003 | Konomura |
| 2004/0015050 | A1 | 1/2004 | Goto et al. |
| 2005/0004434 | A1 | 1/2005 | Bob et al. |
| 2006/0116550 | A1 | 6/2006 | Noguchi |
| 2006/0135851 | A1* | 6/2006 | Yamazaki .......... A61B 1/00137 600/159 |
| 2006/0199999 | A1 | 9/2006 | Ikeda |
| 2006/0252993 | A1 | 11/2006 | Freed |
| 2007/0156018 | A1 | 7/2007 | Krauter et al. |
| 2007/0221701 | A1 | 9/2007 | Ortiz |
| 2007/0282371 | A1 | 12/2007 | Lee |
| 2009/0209820 | A1 | 8/2009 | Tanaka |
| 2009/0286412 | A1 | 11/2009 | Ikeda |
| 2010/0168560 | A1 | 7/2010 | Hauck et al. |
| 2011/0288372 | A1 | 11/2011 | Petersen |
| 2011/0298169 | A1* | 12/2011 | Nguyen ............ A61B 1/00057 269/86 |
| 2011/0313252 | A1 | 12/2011 | Lin |
| 2012/0170767 | A1 | 7/2012 | Astrom et al. |
| 2012/0209068 | A1 | 8/2012 | Hosaka |
| 2014/0046123 | A1* | 2/2014 | Connors ............... A61F 2/0027 600/31 |
| 2014/0148646 | A1 | 5/2014 | Inada |
| 2015/0057537 | A1 | 2/2015 | Dillon et al. |
| 2015/0144215 | A1* | 5/2015 | Bellofatto .............. A61B 1/015 137/625.69 |
| 2015/0173711 | A1 | 6/2015 | Hiraoka |
| 2015/0257634 | A1* | 9/2015 | Nakade ............ A61B 1/00068 600/159 |

FOREIGN PATENT DOCUMENTS

| | | |
|---|---|---|
| CN | 2762381 Y | 3/2006 |
| CN | 102307510 A | 1/2012 |
| CN | 102401995 A | 4/2012 |
| CN | 202748535 U | 2/2013 |
| CN | 103153152 A | 6/2013 |
| CN | 103211566 A | 6/2013 |
| DE | 69 05 185 U | 4/1972 |
| DE | 2954069 C2 | 1/1984 |
| DE | 34 46 698 A1 | 7/1985 |
| DE | 19724261 A1 | 1/1998 |
| DE | 196 27 016 C1 | 2/1998 |
| DE | 19731965 A1 | 1/1999 |
| DE | 19928289 A1 | 1/2001 |
| DE | 10139153 A1 | 2/2003 |
| DE | 697 25 670 T2 | 7/2004 |
| DE | 101 48 099 B4 | 6/2006 |
| DE | 10 2009 060 500 | 7/2011 |
| DE | 102010034623 A1 | 2/2012 |
| DE | 10 2012 009332 | 11/2013 |
| EP | 0 028 396 B1 | 4/1981 |
| EP | 0055394 | 7/1982 |
| EP | 1475031 A1 | 11/2004 |
| EP | 1 759 626 A2 | 3/2007 |
| ES | 2 356 497 | 4/2011 |
| JP | S 48 27116 | 8/1973 |
| JP | S 61 118713 | 6/1986 |
| JP | S 62 227312 | 10/1987 |
| JP | H06254049 A | 9/1994 |
| JP | 10-225439 | 8/1998 |
| JP | H11 244225 | 9/1999 |
| JP | 2001-061772 A | 3/2001 |
| JP | 2001-510696 | 8/2001 |
| JP | 2002-160691 | 6/2002 |
| JP | 2002 291699 | 10/2002 |
| JP | 2003 190085 A | 7/2003 |
| JP | 2005 304 586 A | 11/2005 |
| JP | 2007 111541 A | 5/2007 |
| JP | 2007 252921 | 10/2007 |
| JP | 2007313047 A | 12/2007 |
| JP | 2009 505688 A | 2/2009 |
| JP | 2009 101134 | 5/2009 |
| JP | 2009 530051 A | 8/2009 |
| JP | 2009 201762 | 9/2009 |
| JP | 2010125019 A * | 6/2010 |
| JP | 2012 245058 A | 12/2012 |
| WO | WO 00/13569 A1 | 3/2000 |
| WO | WO 00/33727 | 6/2000 |
| WO | WO 2005/094665 A2 | 10/2005 |
| WO | WO2008056642 A1 | 5/2008 |
| WO | WO 2009/008596 | 1/2009 |
| WO | WO 2011/108157 A1 | 9/2011 |
| WO | WO 2011/114772 A1 | 9/2011 |
| WO | WO 2013/129204 | 9/2013 |

OTHER PUBLICATIONS

Apr. 30, 2015 Int'l Search Report from related PCT App. No. PCT/EP2015/051245 (6 pgs).
Anonymous: "Products I BMP-TAPPI ", , Jun. 30, 2013 (Jun. 30, 2013), XP055394249, Gefunden im Internet: URL:https://web.archive.org/web/20130630082009/http :// www.bmp-tappi.com:80/products [gefunden am Jul. 27, 2017].
Anonymous: "10. Tappo per innesti rapidi femmina", , Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n nesti- rapidifemmina [gefunden am Jul. 27, 2017].
Search Report for Application CN 2014800410593 in 2 pages (English translation).
Search Report for Application CN 201480076051 in 2 pages (English translation).
International Search Report dated Oct. 8, 2014 for International Application No. PCT/EP2014/065587.
International Search Report dated Jan. 13, 2015 for International Application No. PCT/EP2014/073064.
International Search Report dated Jan. 13, 2015 for International Application No. PCT/EP204/073066.
International Search Report dated Jan. 19, 2015 for International Application No. PCT/EP2014/073065.
International Search Report dated Mar. 24, 2015 for International Application No. PCT/EP2014/075902.
International Search Report dated Mar. 2, 2015 for International Application No. PCT/EP2014/077938 in 3 pages.

(56) References Cited

OTHER PUBLICATIONS

International Search Report dated Mar. 24, 2015 for International Application No. PCT/EP2015/051252 in 4 pages.
Second Office Action of corresponding Chinese Patent Application No. 201580005641.9—5 pages (dated May 14, 2018).
Search Report of corresponding Chinese Application No. 2015800056419—4 pages (dated Jan. 22, 2015).
Office Action of corresponding Japanese Patent Application No. 2016-548165—3 pages {dated Aug. 29, 2019).
Office Action of corresponding Chinese Application No. 201580005641.9—14 pages (dated Sep. 4, 2017).

* cited by examiner

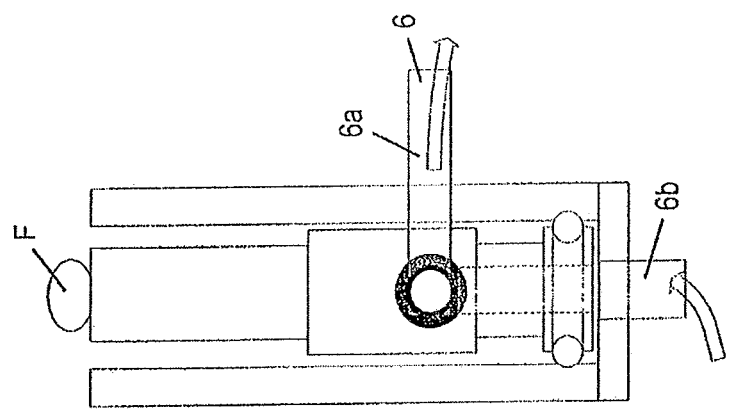
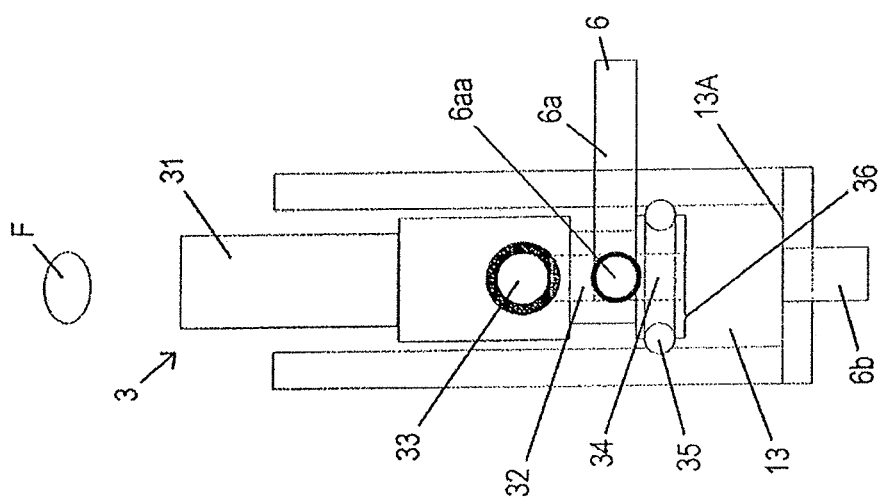

FLUID BLOCK FOR AN ENDOSCOPE CONTROL PART AND ENDOSCOPE

BACKGROUND OF THE INVENTION

Field of the Invention

The present invention relates to a fluid block for an endoscope operating element and an endoscope comprising such a fluid block.

Detailed Description of the Invention

Usually, e.g. a gas-conducting tube for introducing gas, such as an inflation gas, and a liquid-conducting tube for introducing a liquid, such as a rinsing liquid, are provided in an endoscope operating element of an endoscope. In addition, valves for these channels are provided in the endoscope operating element and are used by the user to control the supply of gas/liquid. Sometimes, these valves are very complicated and costly.

This results in the endoscope operating element having many surfaces that may be difficult to clean, thus giving rise to a risk of lasting contamination. Moreover, the assembly and the maintenance of such an endoscope operating element are not easy.

It is therefore the object of the present invention to provide an improved possibility of arranging elements in an endoscope operating element. In addition, an improved endoscope is to be created.

SUMMARY OF THE INVENTION

In respect of the improved possibility of arranging elements of an endoscope operating element, the invention solves this problem by a fluid block comprising the features of claim 1.

An endoscope is shown in claims 13 and 14.

Advantageous further developments form the subject-matters of the dependent claims.

Thus, the invention relates to a fluid block for an endoscope operating element, comprising at least one gas-conducting channel provided inside the fluid block and having an inlet opening and an outlet opening, at least one liquid-conducting channel provided inside the fluid block and having an inlet opening and an outlet opening, and at least one control valve for opening/blocking the at least one gas-conducting channel and the at least one liquid-conducting channel.

The entire fluid circuit for the endoscope can be accommodated in such a fluid block. The only parts required for each channel are a connecting piece for the catheter and a connecting piece that points to the endoscope connector. The assembly and the maintenance of an endoscope operating element comprising such a fluid block is simple and maintenance-friendly.

In the fluid block, the control valve can be arranged in the fluid block such that it is operable from the outside of the fluid block.

In the fluid block, the fluid block can be made of transparent plastic. Such a fluid block can be manufactured at low cost.

In the fluid block, the control valve can be arranged in the at least one gas-conducting channel and in the at least one liquid-conducting channel, wherein the control valve can be switched between a gas-supplying position, in which the control valve opens the gas-conducting channel, and a liquid-supplying position, in which the control valve opens the liquid-conducting channel.

DETAILED DESCRIPTION OF THE PREFERRED EMBODIMENT

In the fluid block, the control valve can be a spool valve slidable to two switching positions, wherein, in the gas-supplying position, the control valve opens the gas-conducting channel and closes the liquid-conducting channel and, in the liquid-supplying position, the control valve opens the liquid-conducting channel and closes the gas-conducting channel; wherein the control valve comprises an air discharge channel which extends in the body of the control valve, whose open outer end points outwards outside of the fluid block and whose inner end communicates with the gas-conducting channel in the gas-supplying position of the control valve.

A working channel having an inlet opening and an outlet opening can be provided inside the fluid block.

In the fluid block, a working channel valve can be arranged adjacent to the control valve such that it is operable from the outside of the fluid block, wherein the working channel valve can be switched between a position in which the working channel is open and a position in which the working channel is closed.

In the fluid block, the control valve and/or the working channel valve can be disposable single-use valves or a disposable single-use valve.

The fluid block can be provided with a channel for at least one electric line for an electronic instrument at the distal end of the endoscope tube, and with channels for pulling cables for the deflecting control.

The features of the invention may be appropriately combined.

Below, the invention is described in detail by way of examples.

BRIEF DESCRIPTION OF THE DRAWINGS

FIG. 5 shows a schematic sectional view of a working channel valve, FIG. 5A showing a position in which the working channel is closed, and FIG. 5B a position in which the working channel is open.

Embodiments of the present invention are described below.

First Embodiment

To start with, a first embodiment is described with reference to FIGS. 1 to 3.

Figure 1:
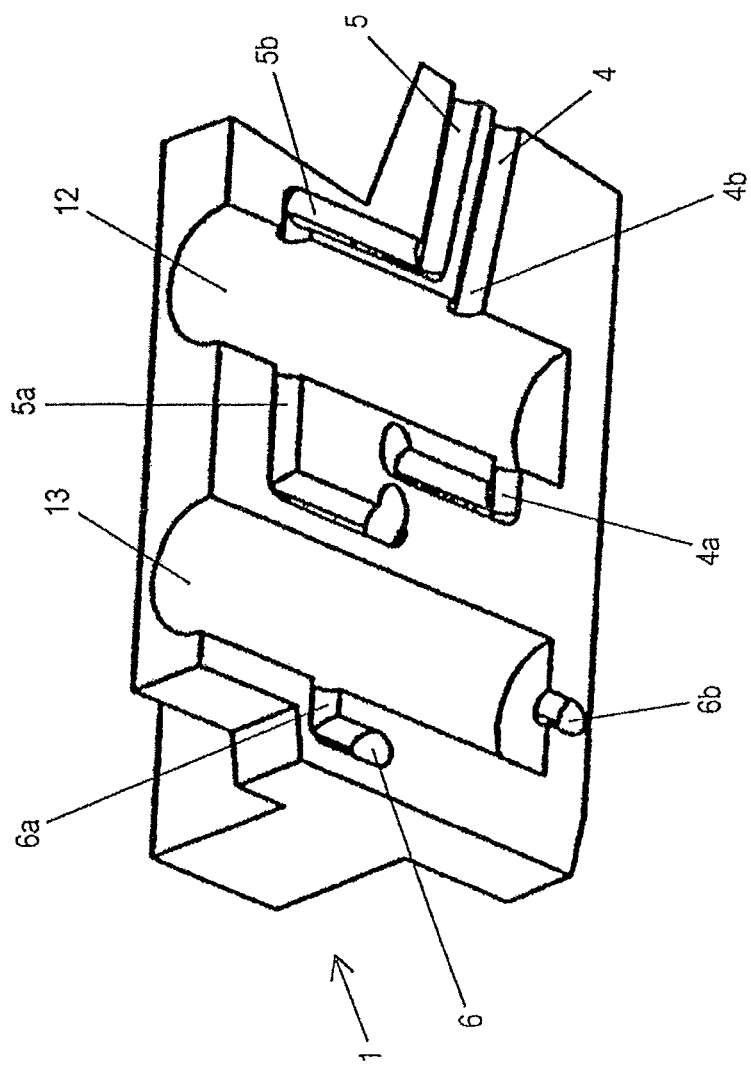
FIG. 1 shows an application example of a fluid block according to the invention.

FIG. 1 shows an application example of a fluid block according to the invention.

In particular, FIG. 1 shows a sectional view of a fluid block 1 according to the invention. The fluid block 1 is made of a preferably transparent plastic material. The fluid block 1 can be produced by casting or molding. The fluid block 1 can also be produced by machining such as milling and drilling. The invention is not limited to a specific manufacturing process.

In the present example, the fluid block 1 is constructed in an approximately rectangular shape and has a proximal side on the left side of FIG. 1 and a distal side on the right side of FIG. 1. The fluid block 1 has an outer shape which matches an inner space of an endoscope operating element described below. To ensure a secure fit in the endoscope operating element, the fluid block 1 can comprise one or more protrusions, such as those shown in FIG. 1 on the side facing away from the viewer. The end face of the protrusion(s) facing away from the fluid block 1 then abuts against an inner wall of the endoscope operating element.

At least one gas-conducting channel 4 and at least one liquid-conducting channel 5 extend through the fluid block 1. In addition, a working channel 6 is provided in the fluid block 1 in the present example.

In the fluid block 1, a cylindrical blind hole 12 is provided for a non-depicted control valve which is described in more detail below such that the blind hole 12 intersects both the gas-conducting channel 4 and the liquid-conducting channel 5. The control valve is activated by the user and selectively blocks and opens both the gas-conducting channel 4 and the liquid-conducting channel 5.

The blind hole 12 divides the gas-conducting channel 4 into a proximal portion 4a and a distal portion 4b, and divides the liquid-conducting channel 5 into a proximal portion 5a and a distal portion 5b. The proximal portions 4a and 5a lead to the endoscope connector and the distal portions 4b and 5b lead to the catheter connection.

Thus, the fluid block 1 comprises an orifice of the gas-conducting channel 4 and an orifice of the liquid-conducting channel 5 at a catheter connecting side of the fluid block 1 and an orifice of the gas-conducting channel 4 and an orifice of the liquid-conducting channel 5 on an endoscope connector side of the fluid block 1. In FIG. 1, the orifice of the distal portion 4b of the gas-conducting channel 4 and the orifice of the distal portion 5b of the liquid-conducting channel 5 are on the right side of the drawing. In other words, the orifice of the distal portion 4b of the gas-conducting channel 4 and the orifice of the distal portion 5b of the liquid-conducting channel 5 are on the distal side of the fluid block 1. The orifice of the proximal portion 4a of the gas-conducting channel 4 and the orifice of the proximal portion 5a of the liquid-conducting channel 5 on an endoscope connector side are not shown in FIG. 1. They can be on the proximal side of the fluid block 1. The invention is not limited thereto. The orifices of the channels can also be arranged on any other side of the fluid block 1.

Moreover, a working channel 6 extends through the fluid block 1.

In the fluid block 1, a cylindrical blind hole 13 is provided for a non-depicted working channel valve, which is described in more detail below, such that the blind hole 13 intersects the working channel 6. Preferably, the blind hole 12 is arranged in parallel and adjacent to the blind hole 13. Thus, the working channel valve is arranged preferably adjacent to the control valve. The working channel valve is activated by the user and selectively blocks and opens the working channel 6.

The blind hole 13 divides the working channel 6 into a proximal portion 6a and a distal portion 6b. The proximal portion 6a leads to the endoscope connector and the distal portion 6b leads to the catheter connection.

Thus, the fluid block 1 has an orifice of the working channel 6 on a catheter connection side of the fluid block 1 and an orifice of the working channel 6 on an endoscope connector side of the fluid block 1. Both orifices are not shown in FIG. 1. The orifices of the working channel 6 can be arranged on any other side of the fluid block 1. Preferably, the orifice of the distal portion 6b is on the distal side of the fluid block 1.

Figure 2:
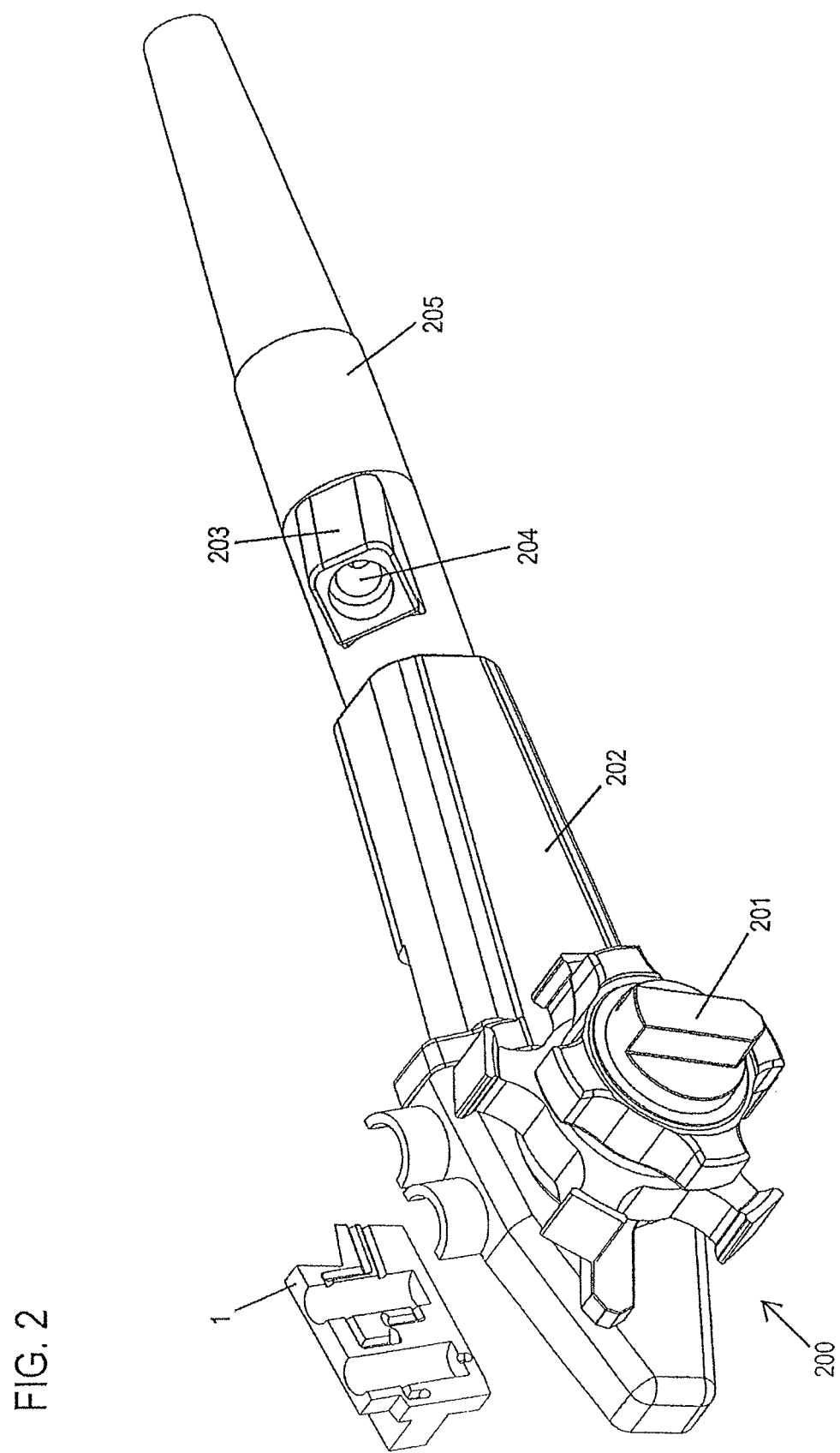
FIG. 2 shows an exploded perspective view of an endoscope operating element including the fluid block of FIG. 1.
Figure 3:
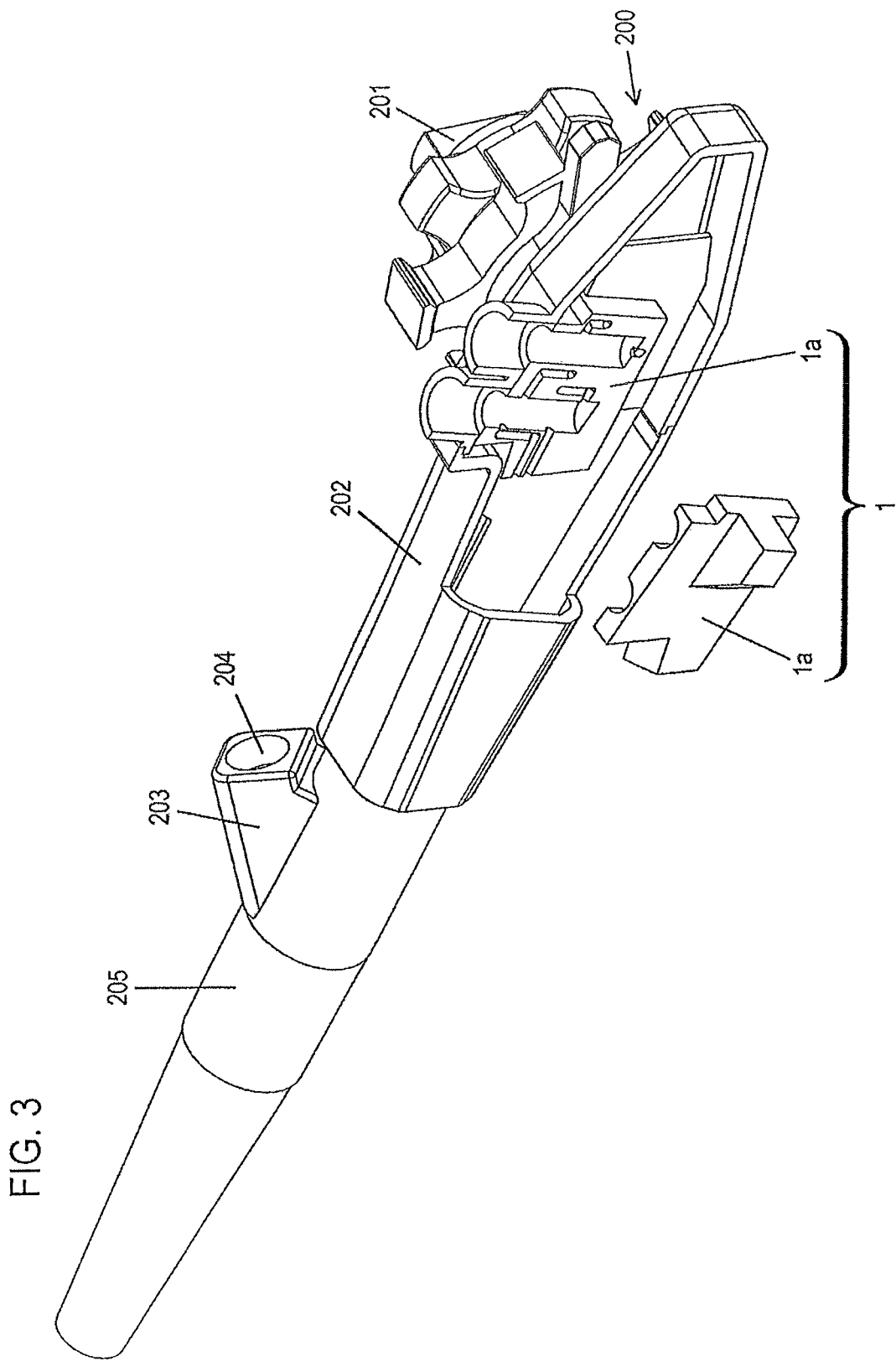
FIG. 3 shows an exploded perspective view of the endoscope operating element including the fluid block of FIG. 2 viewed from the back.

FIG. 2 shows an exploded perspective view of an endoscope operating element having the fluid block of FIG. 1. FIG. 3 shows an exploded perspective view of the endoscope operating element including the fluid block of FIG. 2 viewed from the back.

An endoscope 200 has a control element 201 on an endoscope operating element 202. An access port 203 for a secondary endoscope extends on the distal side of the endoscope handle 202 at a predetermined angle, which may be 45°. The predetermined angle is not limited to 45°.

Distally from the access port 203 for a secondary endoscope, the endoscope 200 has a port 205 for a non-depicted tube element, i.e. a catheter. A centrically provided working channel, which is not shown in FIGS. 2 and 3, runs in the endoscope operating element 202, said working channel continuing in a non-depicted tube element of the endoscope. A working channel branch 204 branches off said working channel into the access port 203. In the access port 203, the working channel branch 204 runs centrically, as well. Thus, the inner outlet of the working channel branch 204 opens into the working channel of the endoscope 200. The inlet of the working channel branch 204 has an opening on the proximal side of the access port 203. A mounting body for the connection with the secondary endoscope is mountable to said opening in a torque-proof manner.

The fluid block 1 can be manufactured as a single fluid block 1 in one piece. As is shown in FIG. 3, the fluid block 1 can also consist of two fluid block counter-pieces 1a, which are attached to each other e.g. by gluing or welding, thus forming the fluid block 1. The left fluid block counter-piece 1a in the representation of FIG. 3 corresponds to the cut-up fluid block shown in FIG. 1.

Second Embodiment

Firstly, a second embodiment is described with reference to FIGS. 4 to 6.

Figure 4C:
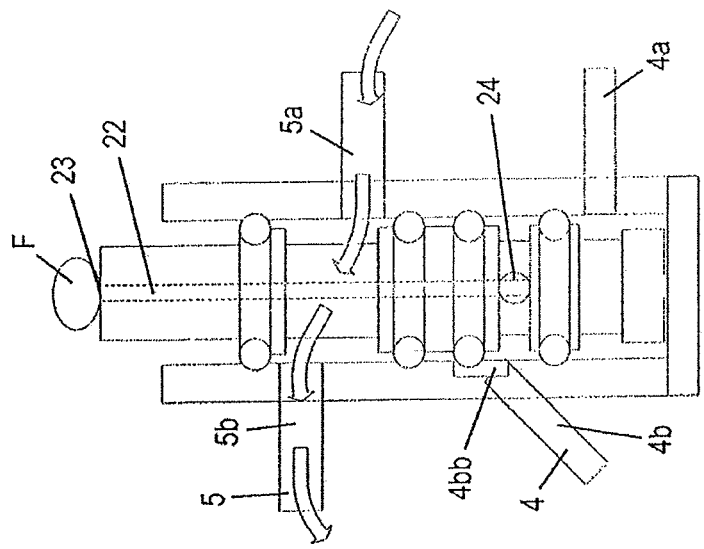
FIG. 4 shows a schematic sectional view of a control valve for opening/blocking a gas-conducting channel and a liquid-conducting channel, FIG. 4A showing an air opening position, FIG. 4B an air-supplying position, and FIG. 4C a flushing position.
Figure 4B:
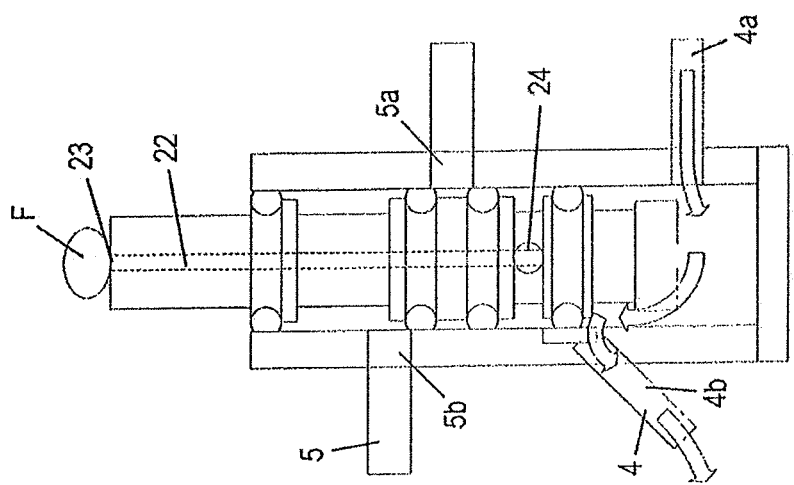
Figure 4A:
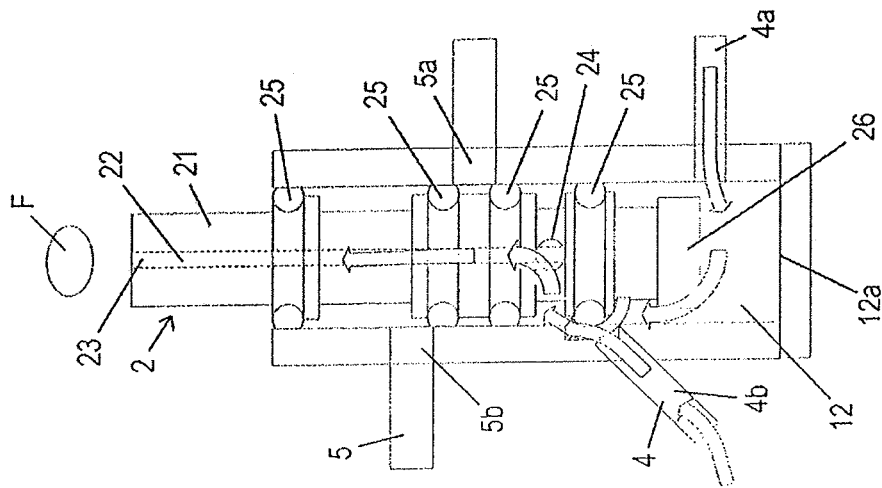

FIG. 4 shows a schematic sectional view of a control valve for opening/blocking a gas-conducting channel and a liquid-conducting channel, FIG. 4A showing an air-opening position, FIG. 4B an air-supplying position and FIG. 4C a flushing position.

In the second embodiment, a fluid block is provided, said fluid block being constructed similarly to the fluid block 1 of the first embodiment.

A control valve 2 shown in FIG. 4 is provided in the blind hole 12 such that it intersects both the gas-conducting channel 4 and the liquid-conducting channel 5. The control valve 2 is activated by the user and selectively blocks and opens both the gas-conducting channel 4 and the liquid-conducting channel 5. The blind hole 12 has a blind hole bottom 12A.

The proximal portion 5a of the liquid-conducting channel 5, the distal portion 5b of the liquid-conducting channel 5, the proximal portion 4a of the gas-conducting channel 4 and the distal portion 4b of the gas-conducting channel 4 end in the blind hole 12. To be more exact, the orifice of the proximal portion 5a of the liquid-conducting channel 5 and the orifice of the distal portion 5b of the liquid-conducting channel 5 are diametrically opposite, but are offset with respect to each other in the longitudinal direction of the blind hole 12, as is shown in FIG. 4A. In addition, the orifice of the proximal portion 4a of the gas-conducting channel 4 and the orifice of the distal portion 4b of the gas-conducting channel 4 are diametrically opposite and are offset with respect to each other in the longitudinal direction of the blind hole 12. When viewed from the blind hole bottom 12A, the channel portions open into the blind hole 12 in the following order: proximal portion 4a of the gas-conducting channel 4, distal portion 4b of the gas-conducting channel 4, proximal portion 5a of the liquid-conducting channel 5 and distal portion 5b of the liquid-conducting channel 5.

The structure of the control valve 2 is described below. The control valve 4 is constructed as a spool valve.

The control valve 2 has an air discharge channel 22 which extends in the cylindrical spool valve body of the control valve 2, whose open outer end 23 points outwardly outside of the fluid block 1 and whose inner end 24 communicates with the gas-conducting channel 4 in the gas-supplying position of the control valve 2. Preferably, the air discharge channel 22 runs centrically inside the spool valve body of the control valve 2. The air discharge channel 22 has an outer section and an inner section. The outer section of the air discharge channel 22 opens to the outside at the outer end 23 and is formed as a blind hole in the spool valve body of the control valve 2. At the inner end of the blind hole, the inner section of the air discharge channel 22 is bent preferably at a right angle to the outer circumferential surface of the spool valve body. The end of the inner section of the air discharge channel 22 at the outer circumferential surface of the spool valve body forms the inner end 24 of the air discharge channel 22. The inner end 24 of the air discharge channel 22 is directed to the inner circumferential surface of the blind hole 12 and is spaced apart therefrom.

The spool valve body of the control valve 2 is provided with seals 25 on its outer circumference at suitable positions, the inner surface of said seals tightly abutting against the outer circumference of the spool valve body and the outer surface thereof tightly abutting against the inner circumference of the blind hole 12. The seals 25 are fixed relative to the control valve 2 and are not moveable.

In the moved-out position of the control valve 2 (see FIG. 4A), a first seal 25 is seated on the outer circumference of the spool valve body such that the first seal is still seated in the blind hole 12. In operation, the control valve 2 is not moved out of the blind hole 12 far enough for the first seal 25 to leave the blind hole 12. A projecting portion 21 of the spool valve body extends between the first seal 25 and the end of the spool valve body pointing upwards in FIG. 4, said end comprising the outer end 23 of the air discharge channel 22.

In the moved-out position of the control valve 2, a second seal 25 that is spaced apart from the first seal 25 is seated at a position on the outer circumference of the spool valve body such that, on the inner circumference of the blind hole, the distal portion 5b of the liquid-conducting channel 5 ends between the first seal 25 and the second seal 25.

In the moved-out position of the control valve 2, a third seal 25 that is spaced apart from the second seal 25 is seated at a position on the outer circumference of the spool valve body such that, on the inner circumference of the blind hole, the proximal portion 5a of the liquid-conducting channel 5 ends between the second seal 25 and the third seal 25.

In the moved-out position of the control valve 2, a fourth seal 25 that is spaced apart from the first seal 25 is seated at a position on the outer circumference of the spool valve body such that, on the outer circumference of the spool valve body, the inner end 24 of the air discharge channel 22 ends between the third seal 25 and the fourth seal 25.

The moved-out position of the control valve 2 is shown in FIGS. 4A and 4B.

As is shown in FIG. 4A, in the moved-out position of the control valve 2, the inner end portion of the spool valve body of the control valve 2 is spaced apart from the blind hole bottom 12A of the blind hole 12.

Preferably, the blind hole 12 has a depression 4bb on its circumferential wall at the point where the distal portion 4b of the gas-conducting channel 4 ends in the blind hole 12. The length of the depression 4bb in the longitudinal direction of the blind hole 12 is longer than the diameter of the fourth seal 25. In the moved-out position of the control valve 2, the fourth seal 25 is positioned at the depression 4bb such that the fourth seal 25 is spaced apart from the end directed outwardly—viewed in the longitudinal direction of the blind hole 12—and from the end of the depression 4bb directed inwardly. Thus, via the depression 4bb, a fluid movement between the area above the fourth seal 25 (the area between the third seal 25 and the fourth seal 25) and the area below the fourth seal 25 (the area between the blind hole bottom 12A and the fourth seal 25) is possible.

In the moved-in position of the control valve 2, the first seal 25 is seated between the outwardly directed open end of the blind hole 12 and the distal portion 5b of the liquid-conducting channel 5.

In the moved-in position of the control valve 2, the second seal 25 is seated below the proximal portion 5a of the liquid-conducting channel 5, the third seal 25 is seated on the outwardly directed end of the depression 4bb at the distal portion 4b of the gas-conducting channel 4, and the fourth seal 25 is seated between the proximal portion 4a of the gas-conducting channel 4 and the distal portion 4b of the gas-conducting channel 4.

The moved-in position of the control valve 2 is shown in FIG. 4C.

Thus, the control valve 2 is a spool valve slidable to two switching positions. The moved-out position of the control valve 2 is a gas-supplying position. The moved-in position of the control valve 2 is a liquid-supplying position. The control valve 2 can be switched between the gas-supplying position and the liquid-supplying position by sliding.

In the gas-supplying position, the fourth seal 25 is at a position below which a communication between the proximal portion 4a of the gas-conducting channel 4 and the distal portion 4b of the gas-conducting channel 4 is made possible. The gas-conducting channel 4 is thus open. In the gas-supplying position, the second seal 25 is positioned below the distal portion 5b of the liquid-conducting channel 5 and above the proximal portion 5a of the liquid-conducting channel 5 and blocks the communication between them. The liquid-conducting channel 5 is thus closed.

In the gas-supplying position, two operating modes are possible.

FIG. 4A shows the air discharge mode. Since, in the air discharge mode, the fourth seal is seated at the depression 4bb such that a fluid movement between the area below the fourth seal 25 and the area above the fourth seal 25 is possible, and the inner end 24 of the air discharge channel 22 is between the third seal 25 and the fourth seal 25, gas, e.g. air, can be discharged from the distal portion 4b of the gas-conducting channel 4 via the air discharge channel 22 to the outside. Even a supply of gas from the proximal portion 4a of the gas-conducting channel 4 does not hinder the gas discharge from the distal portion 4b of the gas-conducting channel 4 via the air discharge channel 22 to the outside.

FIG. 4B shows the inflation mode. The projecting portion 21 of the spool valve body of the control valve 2 projects to the outside and has the outer opening 23 of the air discharge channel 22. The user can close the outer opening 23 of the air discharge channel 22 by a finger F, such as the thumb. The spool valve body of the control valve 2 is seated in the blind hole 12 via the seals 25 and their frictional engagement in a manner secured against sliding such that, when the finger F of the user is pressed against the outer opening 23 of the air discharge channel 22, the spool valve body of the control valve 2 is not pushed into the blind hole 12.

Only when the frictional engagement of the seals 25 with the inner circumference of the blind hole 12 is intentionally overcome, can the spool valve body of the control valve 2 be pushed from the gas-supplying position into the liquid-supplying position.

FIG. 4C shows the liquid-supplying position. The fourth seal 25 is located between the proximal portion 4a of the gas-conducting channel 4 and the distal portion 4b of the gas-conducting channel 4. Thus, the gas-conducting channel 4 is interrupted. Since the orifice of the distal portion 4b of the gas-conducting channel 4 is below the third seal 25 and, thus, a fluid communication between the distal portion 4b of the gas-conducting channel 4 and the inner end 24 of the air discharge channel 22 is possible, gas can still be discharged to the outside through the air discharge channel 22. Between the first seal 25 and the second seal 25, the proximal portion 5a of the liquid-conducting channel 5 and the distal portion 5b of the liquid-conducting channel 5 are in fluid communication. The liquid-conducting channel 5 is thus open.

FIG. 5 shows a schematic sectional view of a working channel valve, FIG. 5A showing a position in which the working channel is closed, and FIG. 5B showing a position in which the working channel is open.

The blind hole 13 of FIG. 5 has a blind hole bottom 13A and comprises an orifice of the distal portion 6b of the working channel 6, which extends downwards in the present example, centrically in the blind hole bottom 13A. The proximal portion 6a of the working channel 6 ends on the inner circumferential surface of the blind hole 13. The proximal portion 6a has an orifice 6aa, as is indicated in FIG. 5.

A working channel valve 3 shown in FIG. 5 is provided in the blind hole 13 such that it intersects the working channel 6. The working channel valve 3 is arranged adjacent to the control valve 2 in the fluid block 1 such that it can be operated from the outside of the fluid block 1, wherein the working channel valve 3 can be switched between a position in which the working channel 6 is open and a position in which the working channel 6 is closed. The working channel valve 3 is operated by the user and selectively blocks and opens the working channel 6.

The exact structure of the working channel valve 3 is described below.

The working channel valve 3 is also constructed as a spool valve. The working channel valve 3 has a cylindrical spool valve body.

The working channel valve 3 has an inner channel 32 arranged in the cylindrical spool valve body of the working channel valve 3. The inner channel 32 has an inlet portion and an outlet portion. The inlet portion of the inner channel 32 is formed as a blind hole and preferably extends centrically inside the spool valve body of the working channel valve 3, and has an inlet opening 34 at the blind hole bottom side of the spool valve body. At the inner end of the inlet portion of the inner channel 32, the inner channel 32 passes into an outlet portion, which is bent to the outer circumferential surface of the spool valve body, preferably at a right angle. The end of the outlet portion of the inner channel 32 at the outer circumferential surface of the spool valve body forms the discharge opening 33 of the inner channel 32. The discharge opening 33 of the inner channel 32 is directed to the inner circumferential surface of the blind hole 13, and is spaced apart therefrom.

On its outer circumference, at an appropriate position at the bottom end (blind hole bottom end) of the spool valve body, the spool valve body of the working channel valve 3 is provided with a seal 35, whose inner surface tightly abuts on the outer circumference of the spool valve body and whose outer surface tightly abuts on the inner circumference of the blind hole 13. The seal 35 is fixed relative to the working channel valve 3 and is not moveable. When the working channel valve 3 is installed in the blind hole 13, the seal 35 is between the distal portion 6b of the working channel 6 and the proximal portion 6a of the working channel 6.

Thus, the working channel valve 3 is a spool valve that can be slid into two switching positions. The moved-out position of the working channel valve 3 is a closed position. The moved-in position of the working channel valve 3 is an open position. The working channel valve 3 can be switched between the closed position and the open position by sliding. In the closed position, the working channel 6 is interrupted. In the open position, the working channel 6 is open, and suction can take place through the working channel 6.

FIG. 5A shows the closed position. In the closed position, the discharge opening 33 of the inner channel 32, which points towards the inner circumferential surface of the blind hole 13, is not in a position opposed to the orifice 6aa of the proximal portion 6a of the working channel 6. For example, the discharge opening 33 of the inner channel 32 has an orifice seal for sealing the edge of the discharge opening 33 of the inner channel 32 against the inner circumferential surface of the blind hole 13.

By pushing the working channel valve 3 inwards towards the blind hole bottom 13A, thereby overcoming the frictional engagement of the seal 35 with the inner circumference of the blind hole 13, the spool valve body of the working channel valve 3 can be slid from the closed position into the open position.

FIG. 5B shows the open position. In the open position, the lower end face of the spool valve body of the working channel valve 3 abuts on the blind hole bottom 13A, wherein, in this position, the discharge opening 33 of the inner channel 32 pointing to the inner circumferential surface of the blind hole 13 is opposed to the orifice 6aa of the proximal portion 6a of the working channel 6. Thus, a fluid communication is possible through the inner channel 32 between the proximal portion 6a of the working channel 6 and the distal portion 6b of the working channel 6. Thus, the working channel 6 is open.

Preferably, the control valve 2 and/or the working channel valve 3 are single-use disposable valves or is a single-use disposable valve. Preferably, the control valve 2 and/or the working channel valve 3 are/is made of molded two-component plastics. Thus, the valves do not constitute a risk of contamination, and no costly cleaning process is required.

Figure 6:
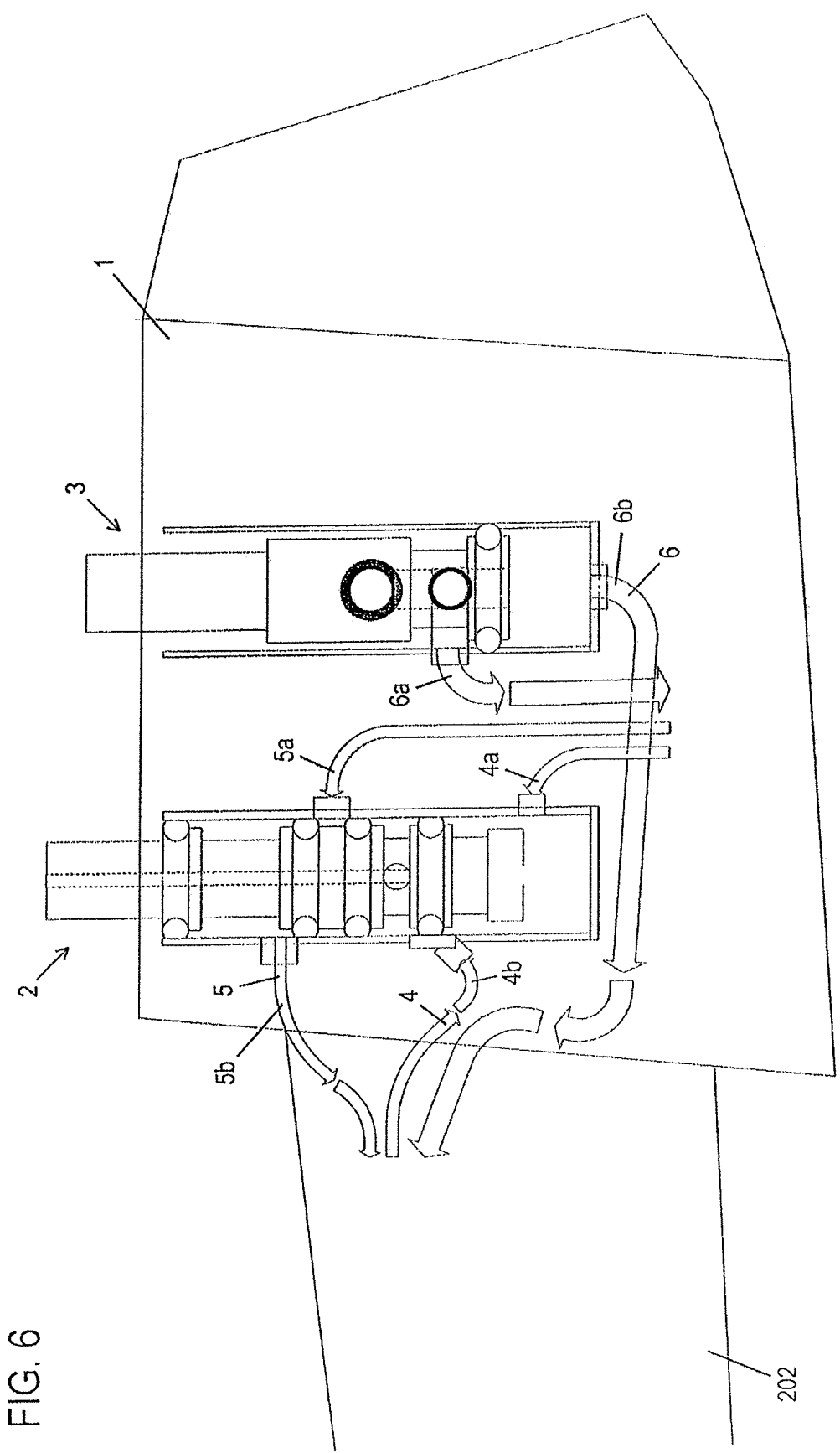
FIG. 6 shows an application example of a fluid block according to the invention, comprising the control valve and the working channel valve of FIGS. 4 and 5.

FIG. 6 shows an application example of a fluid block according to the invention, comprising the control valve and the working channel valve of FIGS. 4 and 5.

The control valve 2 and the working channel valve 3 are provided in parallel and adjacent to each other in the fluid block 1 in their operative positions. Additionally, in FIG. 6, the route of the channels in the fluid block 1 is indicated. From the control valve 2, the distal portion 4b of the gas-conducting channel 4 and the distal portion 5b of the liquid-conducting channel 5 and, from the working channel valve 3, the distal portion 6b of the working channel 6 lead in the fluid block 1 to the distal side. On the distal side, the fluid block 1 has the respective connections of the channels that allow a respective channel continuation through the endoscope operating element 202 to the catheter and to the distal endoscope end. From the control valve 2, the proximal portion 4a of the gas-conducting channel 4, the proximal portion 5a of the liquid-conducting channel 5 and, from the working channel valve 3, the proximal portion 6a of the working channel 6 in the fluid block 1 lead to the proximal side. On the proximal side, the fluid block 1 has the respective connections of the channels that allow a respective channel continuation to the proximal endoscope connector.

Thus, the fluid block 1 only has the proximal and distal channel connections. Therefore, the fluid block 1 can be produced inexpensively, e.g. by a molding process. The assembly is easy. The maintainability of the endoscope operating element 202 is improved.

The fluid block 1 can be arranged in the endoscope operating element 202 formed as a grip piece such that the fluid block 1 is surrounded by a housing section of the endoscope operating element 202. This housing section of the endoscope operating element 202 has an inner shape to which the fluid block 1 is adapted, and has openings through which the projecting portions 21, 31 of the valves 2 and 3 pass.

The fluid block 1 itself may form the grip piece of the endoscope operating element 202 and can be shaped accordingly. If so, no additional housing is required.

Alternatives

In the first and second examples, a gas-conducting channel 4, a liquid-conducting channel 5 and a working channel 6 are provided in the fluid block 1. The number of said channels is not limited. In one fluid block several gas-conducting channels and/or several liquid-conducting channels and/or several working channels can be provided.

In the fluid block, besides the gas-conducting channel 4, the liquid-conducting channel 5 and the working channel 6, one or more channels for one or more electrical line(s) for one or more electronic instrument(s) can be provided at the distal endoscope tube end, and channels for pulling cables for the deflecting control.

In the first and second examples, a blind hole 12 for the control valve 2 and a blind hole 13 for a working channel valve 3 are provided in the fluid block 1. In an alternative, the holes in the fluid block, which are provided for the control valve 2 and the working channel valve 3, may also be through-holes. A valve stop face, as is provided by the blind hole bottom in the examples, can be provided by a cross-sectional constriction in the respective hole or by an inserted pin or an inserted disc, etc.

In a further alternative, through-holes without a valve stop face can be provided. In this case, the valves seated in the holes can reach their valve positions solely from the operator side.

The positions of the channel portions 4a, 4b, 5a, 5b, 6a and 6b in the blind holes can be modified as required and by an appropriate adjustment of the respective valves.

In the embodiments, the holes 12 and 13 for the valves are cylindrical. The holes for the valves may have any shape. Valves having any outer shape can cause cross-sections and shapes in the fluid block that are adapted to said valve outer shapes.

LIST OF REFERENCE SIGNS 1 fluid block
1a fluid block counter-pieces
2 control valve
3 working channel valve
4 gas-conducting channel
4a proximal portion
4b distal portion
4bb depression
5 liquid-conducting channel
5a proximal portion
5b distal portion
6 working channel
6a proximal portion
6aa orifice
6d distal portion
12 blind hole for control valve
12A blind hole bottom
13 blind hole for working channel valve
13A blind hole bottom
21 projecting portion
22 air discharge channel
23 outer opening of the air discharge channel
24 inner opening of the air discharge channel
25 seal
26 valve end portion
31 projecting portion
32 inner channel
33 discharge opening of the inner channel
34 inlet opening of the inner channel
35 seal
36 valve end portion
200 endoscope
201 control element of the endoscope
202 endoscope operating element
203 access port for a secondary endoscope
204 working channel branch in the access port
205 connection for tube element
F finger

What is claimed is:

1. An endoscope comprising an endoscope operating element as a grip piece, wherein the grip piece is formed by a fluid block comprising:

at least one gas-conducting channel provided inside the fluid block and having an inlet opening and an outlet opening, at least one liquid-conducting channel provided inside the fluid block and having an inlet opening and an outlet opening, and at least one control valve for opening/blocking the at least one gas-conducting channel and the at least one liquid-conducting channel, wherein the fluid block comprising two fluid block counter-pieces, which are attached to each other for forming the fluid block, a separation plane between the two fluid block counter-pieces being along a plane containing and parallel to a central axis of the at least one control valve, wherein each of the two fluid block counter-pieces has a part of a space configured for the at least one control valve, and wherein the fluid block being adapted to be inserted into the endoscope operating element of the endoscope.

2. The endoscope according to claim 1, wherein the two fluid block counter-pieces respectively intersect the at least one gas-conducting channel, the at least one liquid-conducting channel, and the at least one control valve, and are attached to each other for forming the fluid block.

3. The endoscope according to claim 1, wherein the two fluid block counter-pieces are attached to each other by gluing or welding.

4. The endoscope according to claim 1, wherein the at least one control valve is arranged in the fluid block such that it is operable from the outside of the fluid block.

5. The endoscope according to claim 1, wherein the fluid block is made of transparent plastic.

6. The endoscope according to claim 1, wherein the at least one control valve is arranged in the at least one gas-conducting channel and in the at least one liquid-conducting channel, wherein the at least one control valve is configured to be switched between a gas-supplying position, in which the at least one control valve opens the at least one gas-conducting channel, and a liquid-supplying position, in which the at least one control valve opens the at least one liquid-conducting channel.

7. The endoscope according to claim 6, wherein the at least one control valve is a spool valve slidable to two switching positions, wherein, in the gas-supplying position, the at least one control valve opens the at least one gas-conducting channel and closes the at least one liquid-conducting channel and, in the liquid-supplying position, the at least one control valve opens the at least one liquid-conducting channel and closes the at least one gas-conducting channel;

wherein the at least one control valve comprises an air discharge channel, which extends in the body of the at least one control valve, whose open outer end points outwards outside of the fluid block and whose inner end communicates with the at least one gas-conducting channel in the gas-supplying position of the at least one control valve.

8. The endoscope according to claim 7, wherein, in the liquid-supplying position of the at least one control valve, a communication between a distal portion of the at least one gas-conducting channel and the inner end of the air discharge channel is possible.

9. The endoscope according to claim 1, comprising a working channel having an inlet opening and an outlet opening and being provided inside the fluid block.

10. The endoscope according to claim 9, wherein, adjacent to the at least one control valve, a working channel valve is arranged in the fluid block such that it is operable from the outside of the fluid block, wherein the working channel valve is switchable between a position in which the working channel is open and a position in which the working channel is closed.

11. The endoscope according to claim 1, wherein the at least one control valve and/or the working channel valve are/is disposable single-use valves/a disposable single-use valve.

12. An endoscope comprising an endoscope operating element as a grip piece, wherein the grip piece is formed by a fluid block comprising:

at least one gas-conducting channel provided inside the fluid block and having an inlet opening and an outlet opening, at least one liquid-conducting channel provided inside the fluid block and having an inlet opening and an outlet opening, and at least one control valve for opening/blocking the at least one gas-conducting channel and the at least one liquid-conducting channel, wherein the fluid block consists of two fluid block counter-pieces, which are attached to each other for forming the fluid block, a separation plane between the two fluid block counter-pieces being along a plane containing and parallel to a central axis of the at least one control valve, wherein the fluid block comprises at least one blind hole, wherein one of the at least one blind hole is configured to receive one of the at least one control valve, each of the two fluid block counter-pieces forms a half of the blind hole, and wherein one of the two fluid block counter-pieces is integrated in a part of the grip piece.

13. An endoscope comprising an endoscope operating element as a grip piece, wherein the grip piece has a housing, wherein in the housing there is disposed a fluid block comprising:

at least one gas-conducting channel provided inside the fluid block and having an inlet opening and an outlet opening, at least one liquid-conducting channel provided inside the fluid block and having an inlet opening and an outlet opening, and at least one control valve for opening/blocking the at least one gas-conducting channel and the at least one liquid-conducting channel, wherein the fluid block consists of two fluid block counter-pieces, which are attached to each other for forming the fluid block, a separation plane between the two fluid block counter-pieces being along a plane containing and parallel to a central axis of the at least one control valve, wherein the fluid block comprises at least one blind hole, wherein one of the at least one blind hole is configured to receive one of the at least one control valve, the fluid block comprising an opening periphery leading into the blind hole, a blind end forming an end of the blind hole away from the opening periphery, and a wall surface extending from the opening periphery to the blind end, wherein each of the two fluid block counter-pieces forms at least a part of the wall surface extending from the opening periphery to the blind end.

* * * * *